United States Patent [19]

Meyer et al.

[11] Patent Number: 5,294,451

[45] Date of Patent: Mar. 15, 1994

[54] FAT SUBSTITUTE COMPOSITIONS HAVING REDUCED LAXATIVE EFFECTS

[75] Inventors: Richard S. Meyer, Federal Way; Michael L. Campbell, Kent, both of Wash.

[73] Assignee: Curtice-Burns, Inc., Rochester, N.Y.

[21] Appl. No.: 857,063

[22] Filed: Mar. 24, 1992

Related U.S. Application Data

[63] Continuation-in-part of Ser. No. 677,553, Mar. 29, 1991, abandoned.

[51] Int. Cl.⁵ ................................................ A23D 9/00
[52] U.S. Cl. ........................................ 426/611; 426/804
[58] Field of Search .......................... 426/611, 804, 575

[56] References Cited

U.S. PATENT DOCUMENTS

| | | | |
|---|---|---|---|
| 2,864,703 | 12/1958 | Schulman | 99/91 |
| 2,864,705 | 12/1958 | Schulman | 99/118 |
| 3,579,548 | 5/1971 | Whyte | 260/410.7 |
| 3,600,186 | 8/1971 | Mattson et al. | 99/1 |
| 3,649,647 | 3/1972 | Ota et al. | 260/345.8 |
| 4,005,195 | 1/1977 | Jandacek | 426/658 |
| 4,005,195 | 1/1977 | Jandacek | 424/180 |
| 4,005,196 | 1/1977 | Jandacek et al. | 424/180 |
| 4,368,213 | 1/1983 | Hollenbach et al. | 426/590 |
| 4,461,782 | 7/1984 | Robbins | 426/612 |
| 4,461,782 | 7/1984 | Robbins et al. | 426/549 |
| 4,469,635 | 9/1984 | Peterson | 260/403 |
| 4,582,715 | 4/1986 | Volpenhein | 426/601 |
| 4,582,927 | 4/1986 | Fulcher | 560/201 |
| 4,668,519 | 5/1987 | Dartey et al. | 426/548 |
| 4,673,581 | 6/1987 | Fulcher | 426/531 |
| 4,678,672 | 7/1987 | Dartey et al. | 426/19 |
| 4,797,300 | 1/1989 | Jandacek et al. | 426/549 |
| 4,840,815 | 6/1989 | Meyer et al. | 426/611 |
| 4,849,242 | 7/1989 | Kershner | 426/601 |
| 4,861,613 | 8/1989 | White et al. | 426/611 |
| 4,880,657 | 11/1989 | Guffey et al. | 426/601 |
| 4,911,946 | 3/1990 | Singer et al. | 426/658 |
| 4,915,974 | 4/1990 | D'Amelia et al. | 426/611 |
| 4,919,964 | 4/1990 | Adams et al. | 426/564 |
| 4,925,692 | 5/1990 | Ryan | 426/531 |
| 4,927,658 | 5/1990 | Klemann et al. | 426/611 |
| 4,927,659 | 5/1990 | Kelmann et al. | 426/611 |
| 4,940,601 | 7/1990 | Orphanos et al. | 426/601 |
| 4,942,054 | 7/1990 | Winter et al. | 426/611 |
| 4,950,140 | 8/1990 | Pflaumer et al. | 424/439 |
| 4,952,687 | 8/1990 | Bodor et al. | 536/119 |
| 4,960,600 | 10/1990 | Kester et al. | 426/310 |
| 4,960,602 | 10/1990 | Talkington et al. | 426/534 |
| 4,962,092 | 10/1990 | Wood, Jr. | 514/23 |
| 4,963,386 | 10/1990 | Klemann et al. | 426/611 |
| 4,973,489 | 11/1990 | Meyer et al. | 426/611 |
| 4,980,191 | 12/1990 | Christensen | 426/601 |
| 4,983,413 | 1/1991 | Meyer et al. | 426/589 |
| 4,992,292 | 2/1991 | Klemann et al. | 426/611 |
| 5,006,351 | 4/1991 | Klemann et al. | 426/611 |
| 5,006,360 | 4/1991 | Howard | 426/601 |
| 5,006,360 | 4/1991 | Howard et al. | 426/601 |
| 5,008,126 | 4/1991 | Klemann et al. | 426/611 |
| 5,085,884 | 2/1992 | Young et al. | 426/611 |
| 5,158,796 | 10/1992 | Bernhardt et al. | 426/549 |

FOREIGN PATENT DOCUMENTS

| | | | |
|---|---|---|---|
| 233856 | 8/1987 | European Pat. Off. | A23D 5/00 |
| 0233856 | 8/1987 | European Pat. Off. | A23D 5/00 |
| 236288 | 9/1987 | European Pat. Off. | A23D 5/00 |
| 0311154 | 4/1989 | European Pat. Off. | C07H 12/06 |
| 0368534 | 5/1990 | European Pat. Off. | A23L 1/308 |
| 0375031 | 6/1990 | European Pat. Off. | A23L 1/308 |

OTHER PUBLICATIONS

Calgene Chemical, Inc. Product Data Sheet, Skokie, Ill., 8 pages.

21 C.F.R. §184.1505, Food and Drug Administration, HHS, Apr. 1, 1992 Edition, p. 476.

Grindsted Brochure, "Emulsifiers for the Baking Industry," 22 pages.

21 C.F.R. §172, Food and Drug Administration, HHS, Apr. 1, 1992 Edition, pp. 74 through 89 (5 copied pages).

R. K. Gupta et al., "Sucrose Esters and Sucrose Ester-/Glyceride Blends as Emulsifiers," *JAOCS* (Apr. 1983), pp. 862–869.

Osipow et al., "Surface Activity of Monoesters . . . Fatty Acid Esters of Sucrose," *Industrial and Engineering Chemistry* (Sep. 1956), pp. 1462–1464.

Kelco Brochure, "Alginates and Xanthan Gum," Copyright 1989, 5 pages.

SPI Group Brochure, "Lecithins As Emulsifiers," Copyright 1987, 7 pages.

Mitsubishi-Kasei Foods Corporation Brochure, "Ryoto Sugar Ester Technical Information Brochure, " Printed Jan. 1991, 29 pages.

SPI Group Publication, "The Lecithin Book," Copyright 1991, 14 pages.

FMC Corporation Bulletin G-34, "Avicel Cellulose Gel (microcrystalline cellulose) Product Description," Copyright 1985, 12 pages.

Grindsted Brochure, "Emulsifiers and Stabilizers for the Food Industry," 38 pages.

Van Den Bergh Food Ingredients Group Product Catalog, Copyright 1990, 20 pages.

Lonza Brochure, "Products for the Food Industry," 11 pages.

*Primary Examiner*—Carolyn Paden

*Attorney, Agent, or Firm*—Christensen, O'Connor, Johnson & Kindness

[57] ABSTRACT

Anti-laxative agents are included in fat substitute compositions to reduce or eliminate anal leakage in mammals of fat substitute materials having a melting point of about 37° C. or less. In one embodiment, the anti-laxative agents are emulsifiers such as polyglyceryl esters of fatty acids; mono- and di-glycerides; microcrystalline cellulose; ethoxylated mono- and di-glycerides; sorbitan esters of fatty acids; glyceryl-lacto esters of fatty acids; acetylated monoglycerides; poly glycerol lactic acid ester; and propylene glycol mono stearate; or gums, such as xanthan gum.

39 Claims, No Drawings

FAT SUBSTITUTE COMPOSITIONS HAVING REDUCED LAXATIVE EFFECTS

CROSS-REFERENCE TO RELATED APPLICATION

This application is a continuation-in-part application of prior copending application Ser. No. 07/677,553, filed Mar. 29, 1991 which is now abandoned.

FIELD OF THE INVENTION

The present invention relates generally to the field of fat substitute compositions, more particularly to those exhibiting reduced laxative effects after ingestion by a mammal.

BACKGROUND OF THE INVENTION

Fats contribute from 30% to 40% of the total calories consumed by most Americans. One of the most common nutritional problems in the United States today is obesity, which results from the consumption of more calories than are expended. Consumption of fat is related to many disease states, such as heart disease. Successful reduction of fat consumption has not been achieved because of the dietary habits of the traditional American. Therefore, the search for fat substitutes or low-calorie fats has attracted attention in recent years.

Among the possible low-calorie fats or fat substitutes synthesized to date are polyglycerol esters, sucrose polyesters (SPE), neopentyl-type alcohols and other sugar derivatives such as sorbitol and mannitol, glycerol dialkyl ethers, triglyceride esters of alpha carboxylic acids, diglyceride esters of short-chain dibasic acids, trialkoxytricarballyate, polydextrose, palatinose, polygalactose, N-oil (tapioca dextrin), microbiologically derived products, nonabsorbable synthetic polymers with properties similar to edible oil, tree-derived products, low-metabolized natural fats and oils, biopolymers, branched polysaccharides and jojoba oil. Many of these are reviewed by Hamm, *J. Food Sci.* 49 419 (1984).

The present inventors have previously discovered a class of fat substitute materials comprising alkyl and hydroxyalkyl glycoside fatty acid polyesters, some of which are disclosed in U.S. Pat. Nos. 4,840,815 and 4,942,054.

Another class of fat substitute materials of note are sucrose fatty acid polyesters, which are disclosed in U.S. Pat. Nos. 3,600,186, 4,368,213, and 4,461,782.

A significant problem associated with the use of liquid fat substitute materials, i.e., those having a melting point at or below body temperature of about 37° C., is an undesired "laxative" effect, which is manifested in leakage of the liquid fat substitute material through the anal sphincter after ingestion. As is common in the art of fat substitute materials, the phrases "laxative effect" and "anal leakage effect" are equivalent terms for the present purposes.

Previously, in U.S. Pat. No. 4,005,195, it has been disclosed that the laxative effect can be reduced or eliminated by combining higher melting material, such as solid triglycerides and solid sucrose polyesters, with the liquid polyesters. Another approach to preventing the undesirable laxative effect is to formulate the fat substitute materials to be completely solid at body temperature.

Completely solid esters and solid triglycerides used as anti-laxative agents have drawbacks when used in low calorie food compositions. For example, the high solids content can result in a "waxy" feel in the mouth when ingested. It would be desirable to have a fat substitute composition that is effective at reducing calories and cholesterol and also has a relatively low solids content, so that it does not feel waxy in the mouth. At the same time, it is also important that the fat substitute composition not exhibit the laxative side effect.

Accordingly, one object of the present invention is to provide agents that exert an anti-laxative effect when used in combination with fat substitute materials in foods.

It is yet another object of the present invention to provide new methods for reducing the laxative side effects associated with fat substitute materials as compared to the prior art.

The above and other objects of the present invention as will hereinafter become more readily apparent have been achieved by the present invention, which is disclosed in detail herein.

SUMMARY OF THE INVENTION

The present invention relates to the discovery by the present inventors of new ways to reduce the laxative or anal-leakage effect of nondigestible liquid fat substitutes. In one embodiment, the inventors discovered that polyol fatty acid polyesters having three or fewer ester groups, which are at least partially digestible, can serve effectively as anti-laxative agents. In another embodiment of this invention, the inventors discovered that various types of emulsifiers and gums can also exert an anti-laxative effect when used with fat substitute materials.

The following are exemplary anti-laxative agents of this invention: polyglycerol esters of fatty acids (in bead form) [PGE]; polyglycerol esters of fatty acids (in plastic form) [PGE]; sucrose mono-, di-, and tri-polyesters; mono- and di-glycerides (in solid form) [MDG]; microcrystalline cellulose (i.e., avicel); ethoxylated mono-, di-glycerides (e.g., Durfax EOM) [EMD]; monoglyceride (in bead form) (e.g., Dimodan PVK) [MG]; sorbitan esters of fatty acids (e.g., Famodan MS VEG) [SEFA]; glyceryl-lacto esters of fatty acids (in solid form) (e.g., Durlac 100 W) [GLE]; acetylated monoglycerides (e.g., Cetodan); poly glycerol lactic acid ester (e.g. Lactodan); propylene glycol mono stearate; and xanthan gum. Thus, the present invention is directed to fat substitute compositions, which comprise a fat substitute material and an anti-laxative agent as described herein, methods of reducing anal leakage resulting from ingestion of food compositions containing fat substitute materials, and to low calorie food compositions containing the fat substitute compositions.

DETAILED DESCRIPTION OF THE PREFERRED EMBODIMENT

Terminology

The fat substitute materials useful in connection with the present invention may vary widely in chemical structures, but all of them can be described as edible, fat-like materials that are liquids at body temperature and, thus, exhibit an anal leakage or laxative effect after ingestion. In one preferred embodiment, these materials are polyol fatty acid polyesters. Such materials are referred to herein by the equivalent terms: "polyol fatty acid polyester fat substitute materials," or "polyol fat substitute materials." In another preferred embodiment, these materials are dicarboxylic acid esters based on malonic acid. These materials are referred to herein as "dicarboxylic acid ester fat substitute materials." Other specific fat substitute materials that may be used in connection with this invention are: esterified propoxylated glycerols, such as those described in U.S. Pat. No. 4,861,613; polysiloxanes, such as those described in U.S. Pat. No. 4,983,413; complex linked esters, such as those described in U.S. Pat. No. 4,963,386; polyvinyl oleates, such as those described in U.S. Pat. No. 4,915,974, and the like. Each of the U.S. patents cited herein is incorporated in its entirety herein by reference. The expression "fat substitute material" is used to refer to all of these various types of materials, insofar as they are edible, fat-like materials that are liquids at body temperature. Typically, such fat substitutes will also be at most partially digestible (and preferably substantially nondigestible). Although the present disclosure is preferably directed to human usage, such that body temperature is ca. 37° C., veterinary usages are also contemplated. In the case of veterinary embodiments, the present invention is expected to be applicable when the fat substitute materials cause an anal leakage or laxative effect when fed to an animal, preferably a mammal. Mixtures of fat substitute materials are also contemplated in connection with the present invention. A more detailed description of the fat substitute materials is provided below under the heading "Fat Substitute Materials."

As noted above, when the fat substitute materials are liquid at body temperature, they have a tendency to cause an undesirable so-called laxative effect, i.e., leakage of the liquid fat substitute material through the anal sphincter. This effect is referred to herein as the "laxative effect" or the "anal leakage effect."

The agents that are used to reduce or eliminate the laxative effect of the fat substitute materials of this invention are referred to herein as "anti-laxative agents" or "anti-anal leakage agents". These agents are capable of reducing or preventing frank leakage of the fat substitute materials; the natural stool-softening effect of the fat substitute materials may not be substantially affected, but this latter effect is not a significant problem.

The combination of a fat substitute material with an anti-laxative agent is referred to as a "fat substitute composition" herein.

Inclusion of a fat substitute composition of the present invention into a food results in a "low calorie food composition." These food compositions will provide the benefits of low caloric content while causing reduced or, preferably, eliminated laxative side effects in a mammal after ingestion of the low calorie food compositions.

Anti-Laxative Agents

The present inventors have discovered that certain compounds that possess emulsification properties exhibit an anti-laxative effect when used in combination with fat substitute materials. In a first preferred embodiment of this invention, the anti-laxative agents are edible, digestible polyol fatty acid polyesters, which differ from the polyol fat substitute materials in that the anti-laxative agents contain three or fewer esterified hydroxyl groups and are at least partially digestible. Therefore, these mono-, di-, and tri-fatty acid esters of a polyol are not considered fat substitute materials. Because the anti-laxative agents possess both hydrophilic and hydrophobic groups, these compounds may be classified as amphipathic molecules, which have emulsification properties. To exert the anti-laxative effect, these polyol fatty acid polyesters are typically non-liquid at 37° C.

In broad terms, the above-described anti-laxative agents are polyols, especially sugars or sugar alcohols esterified with three or fewer fatty acid groups. The polyol may be a monosaccharide, a disaccharide, or a higher saccharide (e.g., a trisaccharide, etc.). Preferred polyols for preparing the polyesters that are useful as anti-laxative agents in the present invention are selected from the group consisting of glucose and sucrose. The sugar may be in the form of a glycoside, wherein an alkyl or hydroxyalkyl group is present on the anomeric carbon of the sugar residue. For example, when the sugar is glucose, the glycoside is a glucoside. The alkyl and hydroxyalkyl residues will typically have from about 1 to about 18 carbon atoms, preferably 1 to 12 carbon atoms; the hydroxyalkyl residues will typically contain from 1 to 4 hydroxyl groups.

The anti-laxative polyols are esterified on three or fewer of the polyol hydroxyl groups with a fatty acid. Of the mono-, di-, and tri-esters, the mono-and di-esters are preferred because of their greater emulsification properties. The di- or tri-esters may contain multiple identical fatty acids, or they can all be the same. The fatty acid preferably has from about 8 to about 18 carbon atoms and may be straight chain, branched, cyclic, or a mixture thereof. Although both saturated and unsaturated fatty acids are possible, the fatty acids are preferably saturated.

Specific nonlimiting examples of the above type of anti-laxative agent are the following: sucrose mono-, di-, and tri- palmitates and stearates, and methyl glucoside mono-, di-, and tri- palmitates and stearates.

In another embodiment of this invention, the present inventors have discovered that certain other compounds, which can be characterized as either emulsifiers or gums, have an anti-laxative effect when combined with a fat substitute material. Specific anti-laxative agents of the emulsifying type are: polyglyceryl esters of fatty acids (beads) [PGE]; polyglyceryl esters of fatty acids (plastic) [PGE]; mono- and di-glycerides (solid) [MDG]; microcrystalline cellulose; ethoxylated mono-, di-glycerides (e.g., Durfax EOM) [EMD]; monoglyceride (bead) (e.g., Dimodan PVK) [MG]; sorbitan esters of fatty acids (e.g., Famodan MS VEG) [SEFA]; glyceryl-lacto esters of fatty acids (solid) (e.g., Durlac 100 W) [GLE]; acetylated monoglycerides (e.g., Cetodan, available from Grindsted Chemical Corp.); poly glycerol lactic acid ester (e.g., Lactodan, available from Grindsted Chemical Corp.); and propylene glycol mono stearate. These compounds are distinct from the bulking agents which have previously been disclosed as useful in combination with fat substitute materials in U.S. Pat. No. 4,797,300.

Gums have also been found effective as anti-laxative agents. A specific gum found suitable as an anti-laxative agent is xanthan gum, preferably when used at levels of at least about 20% by weight of the fat substitute material.

By "polyglyceryl esters of fatty acids" is meant molecules containing from 3 to 10 glyceryl groups esterified to 1 to 10 $C_1$–$C_{18}$ fatty acids. These compounds should also be non-liquids at room temperature to exert a sufficient anti-laxative effect. Those polyglyceryl esters of fatty acids that are in bead or plastic form at room temperature are effective anti-laxative agents, whereas those that are liquids at room temperature are not.

By "mono- and di-glycerides" is meant molecules containing one glyceryl group esterified to one or two $C_1$-$C_{18}$ fatty acids. These compounds should also be non-liquids at room temperature to exert a sufficient anti-laxative effect. An example is Dur Em 207 E (bead form).

"Microcrystalline cellulose" is derived from crystallite zones found in regenerated, mercerized and alkali celluloses. By applying a chemical pretreatment to destroy molecular bonds holding these crystallite zones, followed by mechanically treating to disperse the crystallites in aqueous phase, smooth, colloidal, microcrystalline cellulose gels with useful functional and rheological properties are produced. An exemplary material is Avicel cc691, which is a mixture of microcrystalline cellulose and carboxy-methyl cellulose.

"Ethoxylated mono- and di-glycerides" are molecules containing one glyceryl group esterified to one or two $C_1$-$C_{18}$ fatty acids, wherein 1 or 2 ethoxylate moieties are bonded to the glyceryl group by means of an ether linkage. An example is Durfax TM EOM.

"Sorbitan esters of fatty acids" are made up of sorbitan esterified to 1 to 4 $C_1$-$C_{18}$ fatty acids. One example is Famodan TM MS VEG.

"Glyceryl-lacto esters of fatty acids" are made up of lactic acid esterified to a glyceryl group, and also, from 1 to 3 $C_1$-$C_{18}$ fatty acids esterified to the molecule. One example is Durlac TM 100 W.

In preferred embodiments, the fatty acids in the above compounds are $C_{12}$-$C_{18}$ saturated acids.

The above anti-laxative agents are usually incorporated into the fat substitute compositions in an effective amount of from about 10% to about 50% by weight based on the weight of the fat substitute material. Preferably, the amount will be from about 10% to about 30%, and most preferably from about 15% to about 25%. The anti-laxative agent typically constitutes from about 0.5 to 10% by weight of the overall low calorie food composition. Mixtures of one or more of the above-described fat substitute materials and/or anti-laxative agents may be incorporated into the fat substitute composition, where desired.

Fat Substitute Materials

The following are some representative fat substitute materials, which are included for illustrative purposes.

In a first embodiment, the fat substitute materials of the present invention are edible, non-digestible polyol fatty acid polyesters that cause a laxative effect when ingested by a mammal. The polyester fat substitutes that cause the laxative effect are those that are liquid at body temperature (e.g., 37° C. for humans). Preferred polyol fatty acid polyester fat substitute materials are sugar fatty acid polyesters, and sugar alcohol fatty acid polyesters. Preferred polyol fat substitute materials are sucrose polyesters and alkyl/hydroxyalkyl glycoside polyesters. The sugars will typically contain from 4 to 8 hydroxyl groups.

Sugar and sugar alcohol fatty acid polyesters comprise sugar moieties and fatty acid moieties. The term "sugar" is used as generic to mono-, di-, and trisaccharides, and to both reducing or nonreducing sugars. The term "sugar" includes glycosides derived from reducing sugars, e.g., alkyl and hydroxyalkyl glycosides. The term "sugar alcohol" is used as generic to the reduction product of sugars in which the aldehyde or ketone group has been reduced to an alcohol. The fatty acid ester compounds are prepared by reacting a monosaccharide, disaccharide, trisaccharide, sugar alcohol, alkyl glycoside or hydroxyalkyl glycoside with a fatty acid as described previously, e.g., in U.S. Pat. Nos. 4,973,489; 4,942,054; and 4,840,815, which are hereby incorporated by reference.

Examples of suitable monosaccharides are those containing four hydroxyl groups, such as xylose, arabinose, and ribose; the sugar alcohol derived from xylose, i.e., xylitol, is also suitable. The monosaccharide erythrose is not suitable as the fat substitute material since it only contains three hydroxyl groups; however, the sugar alcohol derived from erythrose, i.e., erythritol, contains four hydroxyl groups and is thus suitable. Among five hydroxyl-containing monosaccharides that are suitable for use herein are glucose, mannose, galactose, fructose, and sorbose. A sugar alcohol derived from sucrose, glucose, or sorbose, e.g., sorbitol, contains six hydroxyl groups and is also suitable as the alcohol moiety of the fatty acid ester compound. Examples of suitable disaccharides are maltose, lactose, and sucrose, all of which contain eight hydroxyl groups. An example of a suitable trisaccharide is raffinose.

In preparing sugar or sugar alcohol fatty acid polyesters of the present invention a sugar or sugar alcohol compound such as those identified above may also be esterified with one type or a mixture of fatty acids having from about 8 to about 18 carbon atoms. Examples of suitable fatty acids are caprylic, capric, lauric, myristic, myristoleic, palmitic, palmitoleic, stearic, oleic, ricinoleic, linoleic, and linolenic. The fatty acids can be derived from naturally occurring or synthetic fatty acids and can be saturated or unsaturated, including positional and geometric isomers.

Fatty acids per se or naturally occurring fats and oils can serve as the source for the fatty acid component of the polyester fat substitute material. For example, $C_{16}$-$C_{18}$ fatty acids can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component.

The polyol fatty acid polyesters (both those suitable for use as fat substitute materials and as anti-laxative agents) can be prepared by any of a variety of methods well known to those skilled in the art. These methods include: transesterification of the sugar or sugar alcohol with methyl, ethyl or glycerol fatty acid esters using a variety of catalysts; acylation of the sugar or sugar alcohol with a fatty acid chloride; acylation of the sugar or sugar alcohol with a fatty acid anhydride; and acylation of the sugar or sugar alcohol with a fatty acid per se. As an example, the preparation of sugar and sugar alcohol fatty acid esters is described in U.S. Pat. No. 2,831,845, incorporated herein by reference. Other examples of suitable reactants, procedures and conditions may be found in U.S. Pat. Nos. 4,973,489; 4,942,054; and 4,840,815, each of which is also incorporated by reference herein.

Two important features of the polyester fat substitute materials useful in this invention are that they predominantly contain at least four fatty acid polyester groups and that they melt at 37° C. or less. Polyol fatty acid polyester compounds that contain four or more fatty acid ester groups are digested very little if at all and thus have desirable low calorie properties for use as fat substitutes. In contrast, polyol fatty acid polyester compounds that contain three or fewer fatty acid ester groups are digested in the intestinal tract much in the manner as ordinary triglyceride fats; they are useful as anti-laxative agents but not as fat substitutes.

Preferred polyol fat substitute materials for the purposes of this invention are sucrose fatty acid polyesters. Especially preferred sucrose fatty acid polyesters have the majority of their hydroxyl groups esterified with fatty acids. Preferably at least about 85%, and most preferably at least about 95%, of the sucrose fatty acid polyesters are selected from the group consisting of octaesters, heptaesters and hexaesters, and mixtures thereof. Preferably, no more than about 35% of the esters are hexaesters or heptaesters, and at least about 60% of the sucrose fatty acid polyesters are octaesters. Most preferably, at least about 70% of the sucrose polyesters are octaesters.

Other preferred polyol fat substitute materials are alkyl or hydroxyalkyl glycoside fatty acid polyesters. Alkyl/hydroxyalkyl glycosides are the reaction products of a reducing mono-, di-, or trisaccharide with a monohydric, dihydric, trihydric or tetrahydric alcohol having from 2 to 18 carbons (excluding carbon atoms contained in any hydroxyl protecting groups used in synthesizing the esters). The fatty acid portion of the alkyl glycoside preferably has 4 to 18 carbon atoms. These fatty acids may be saturated, unsaturated, straight chain, branched, cyclic, or a mixture thereof. The preferred glycosides are formed of glucose, galactose, lactose, or maltose and ethanol, propanol, monohydroxyl protected propanediol, or dihydroxy protected glycerol. The dihydroxy protected glycerol is preferably 1,2-isopropylidene glycerol or 1,3-benzylidene glycerol.

In a second embodiment, the fat substitute materials are edible, non-digestible dicarboxylic acid esters, such as those previously disclosed in U.S. Pat. Nos. 4,673,581 and 4,582,927, which are hereby incorporated by reference. These esters have the general formula:

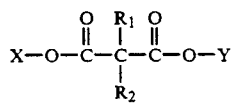

wherein $R_1$ and $R_2$ are H or $C_1$-$C_{20}$ alkyl groups and X and Y are $C_{12}$-$C_{18}$ alkyl, alkenyl, or dienyl groups. These compounds are synthetic oils or low-melting solids (i.e., they have a melting point of about 37° C. or less).

Preferably, at least one R group is a $C_1$-$C_{20}$ alkyl group and the other R group is hydrogen or a $C_1$-$C_{20}$ alkyl group. In particularly preferred compounds, one R group is hydrogen and the other R group is a $C_{16}$-$C_{18}$ alkyl group, or both R groups are $C_{16}$-$C_{18}$ alkyl groups.

The X and Y groups are preferably $C_{14}$-$C_{18}$ alkyl, alkenyl or dienyl groups.

Two exemplary fat substitutes of this type are hexadecyl dioleylmalonate and dihexadecyl dioleylmalonate.

Exemplary fatty alcohols suitable for use in this embodiment of the invention are oleic, myristic, linoleic, palmitic, and stearic alcohols. Suitable acids are malonic, monoalkylmalonic, and dialkylmalonic acids. Mixtures of these fat substitutes may be utilized where desired.

In a third embodiment, esterified propoxylated glycerols are employed as the fat substitute materials. These molecules have the following exemplary formula:

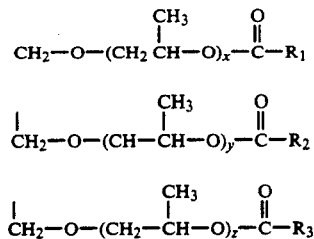

wherein $x+y+z \geq 5$, and $R_1$, $R_2$, and $R_3$ are independently selected from fatty acids. Preferably, the fatty acids are $C_8$-$C_{24}$ moieties, which may be straight chain, branched, saturated or unsaturated.

In a fourth embodiment, the fat substitute material is a complex linked ester, having the following exemplary formula:

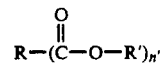

wherein R is a linking covalent bond or saturated or unsaturated aliphatic group; n is 2 to 6; and the R' groups comprise residues defined by the following formula:

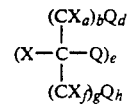

where:
C is a carbon atom;
X is a bridging bonding valence, hydrogen, or substituted or unsubstituted lower aliphatic group (e.g., $C_1$-$C_4$), the various X groups being the same or different;

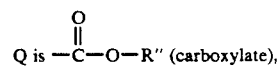

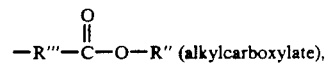

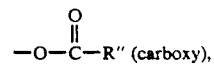

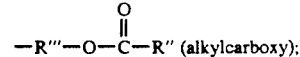

—O—R" (alkoxy), or —R'"—O—R" (alkylalkoxy) radicals; with the proviso that at least one of the Q radicals be other than carboxy;
R" is a substituted or unsubstituted aliphatic group, containing, for example, no more than 30 carbons, e.g.,

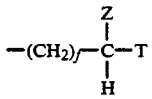

the various R' and R" groups, respectively, being the same or different;

R''' is a lower alkylene, desirably methylene or ethylene, preferably methylene, group which can be the same or different;

T is hydrogen or a substituted or unsubstituted aliphatic group, e.g., no greater than 22 carbons, containing 0 to 5 unsaturated linkages (e.g., C=C double bonds, C≡C triple bonds) per T residue;

Z is a bridging bonding valence, hydrogen, or an alcohol, glycol, ester, e.g.,

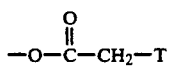

ether, or the like, residue;

with the proviso that there is only one bridging bonding valence per R' group;

and where:
a=0 to 3, preferably 0 to 2;
b=0 to 4, preferably 0 to 1;
d=1 or 2;
e=0 to 5, preferably 1 to 2;
f=0 to 3, preferably 0 to 2;
g=0 to 4, preferably 0 to 1;
h=1 or 2;
j=0 to 10, preferably 0 to 3.

Preferably, each R' group will contain from 2 to 3, most desirably 2, Q radicals.

In a fifth embodiment, the fat substitute may be a polysiloxane, having the following exemplary formula:

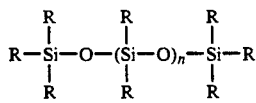

wherein each R is independently selected from $C_1$-$C_6$ lower alkyl, phenyl, preferably methyl and/or phenyl, and n ranges from 1 to 100.

In a sixth embodiment, the fat substitute material is polyvinyl alcohol esterified with fatty acids. Preferably, the polyvinyl alcohol backbone has a molecular weight of from 500 to 8000, particularly preferably, 1000 to 5000. The fatty acids are preferably $C_4$-$C_{30}$, straight chain or branched, saturated or unsaturated. $C_{10}$-$C_{22}$ fatty acids are preferred. Especially preferred is the unsaturated fatty acid oleic acid.

Other exemplary fat substitute materials suitable for use in connection with this invention are trialkoxycarballyates and polydextroses.

It is to be understood that the above embodiments of the fat substitute materials are only examples of the range of fat substitute materials that can be used in connection with the present invention. That is, the present anti-laxative agents are contemplated to be useful with any fat substitute material that is a liquid at body temperature and creates an anal leakage problem upon ingestion. These fat substitute materials should also be "fat-like" in terms of mouth feel and physiochemical properties (e.g., rheology, viscosity, and the like).

Low Calorie Food Compositions

The fat substitute compositions comprising the fat substitute materials and the anti-laxative agents can be used as a partial or total replacement for normal fats in any fat-containing food to provide low calorie benefits. The amount of the fat substitute composition to be substituted for the fat ingredients to produce a low calorie food depends on the application. In most cases, greater than 10% of the fat ingredients are replaced with the fat substitute composition to achieve meaningful calorie reduction. Up to 100% of the fat ingredients of a food can be substituted with the fat substitute compositions of the present invention. However, it is recognized that fat ingredients provide many essential nutrients in human and animal diets. For example, fat ingredients in foods provide fatty acids, which are precursors of the prostaglandins as well as being carriers for fat-soluble vitamins. It is therefore preferred that less than 100% of the fat ingredients be replaced by the fat substitute compositions of the instant invention in any one food product. Accordingly, it is preferred that from 25% to 85% of the fat ingredients in a food be replaced with a fat substitute composition according to the present invention. Particularly preferably 33% to 75% of the fat ingredients are replaced with a fat substitute composition.

Incorporation of the fat substitute compositions of the present invention may be carried out by including a measured quantity thereof to a foodstuff or by cooking (e.g., frying) the foodstuff in the fat substitute compositions, etc.

Methods of Reducing Anal Leakage

Also provided by the present invention are methods of reducing anal leakage in a mammal after ingestion by the mammal of a food composition comprising the fat substitute compositions of the present invention. Essentially, the method involves incorporating an amount of one or more of the anti-laxative agents described hereinabove effective to reduce or eliminate anal leakage of the fat substitute material. The effective amount of the anti-laxative agent is described above. Preferably the anti-laxative agent will be added to the fat substitute material to form a fat substitute composition prior to addition to the food. However, the anti-laxative agent could be added to the food before or after a fat substitute material is included in the food.

The following examples are intended to be illustrative of the present invention and to teach one of ordinary skill how to make and use the invention. These examples are not intended in any way to limit the invention or otherwise limit the protection afforded by Letters Patent hereon.

EXAMPLE I

An emulsifier feeding study was conducted to determine disposition of anal leakage in rats.

Rats

Species—Sprague Dawley; Weight—150 to 250 g; Sex—Female

Feed

Teklad rat chow (fat free)—granular

The feed is admixed with Sucrose Polyesters (Oleate) at a level of 16% as the fat substitute material. Of the 16% SPE-Oleate, 20% consists of the specific emulsifier, respectively.

Emulsifiers

The following were the emulsifiers tested:
Poly Glyceryl Esters of Fatty Acids (liquid) [PGE];
Poly Glyceryl Esters of Fatty Acids (beads) [PGE];
Poly Glyceryl Esters of Fatty Acids (plastic) [PGE];
Sucrose Polyesters (mixture of mono-, di-, and tri-esters) [DK20];
Polypropylene Alginate [PPA];
Mono- and Di- Glycerides (solid) [MDG];
Locust Bean Gum [Loc. Bean];
Carboxy Methyl Cellulose [CMC]; and
Avicel cc691.

Controls

Sucrose Polyester (Oleate) [SPE]; Peanut Oil

Scoring

The degree of anal leakage is determined on a scale of 0 to 4, defined as follows:

0=None; 1=Trace; 2=Slight; 3=Moderate; 4=Severe

Those compounds that rated less than one are preferred as anti-laxative agents. Those that rated 1 or slightly above one can also be used as anti-laxative agents. Scoring was conducted twice daily.

The results are reported in the following Table 1:

TABLE 1

| DIET | AVERAGE SCORE | % EFFECTIVENESS |
|---|---|---|
| 1. PGE (liquid) | 1.18 | 70.50 |
| 2. PGE (beads) | 0.33 | 91.75 |
| 3. PGE (plastics) | 0.69 | 82.75 |
| 4. DK20 - SPE | 0.49 | 87.75 |
| 5. PPA | 2.22 | 44.50 |
| 6. MDG (solid) | 0.18 | 95.50 |
| 7. Loc. Bean | 2.07 | 48.25 |
| 8. CMC | 1.62 | 59.5 |
| 9. Avicel 691 | 1.00 | 75.00 |
| 10. SPE - Control | 2.59 | 35.25 |
| 11. Peanut Oil - Control | 0.00 | 100.00 |

EXAMPLE II

An emulsifier feeding study was done to determine disposition of anal leakage in rats.

Rats

Species—Sprague Dawley; Weight—150 to 250 g; Sex—Female

Feed

Teklad rat chow (fat free)—granular

The feed was admixed with Sucrose Polyesters (Oleate) at a level of 16% as the fat substitute material. Of the 16% SPE-Oleate, 20% consists of the specific emulsifier, respectively, except that in the case of the mono-, di- glycerides, 10% consists of the specific emulsifier.

Emulsifiers

The following are the emulsifiers tested:
Lecithin - Alcolec F100;
Mono-, Di- Glyceride (solid) 10% - Dur Em 207E Beads [MD];
Ethoxylated Mono-, Di- Glycerides - Durfax EOM [EMD];
Polysorbate 60- Durfax 60K [Poly 60];
Sodium Stearoyl Lactolate - Artodan SP55K [SSL];
Mono- Glyceride (soft plastic) - Dimodan LSK [MG];
Mono- Glyceride (plastic) - Dimodan CPK [MG];
Mono- Glyceride (bead) - Dimodan PVK [MG];
Sorbitan Esters of Fatty Acids - Famodan MS VEG [SEFA];
Diacetyl Tartaric Acid Esters of Mono Glycerides - Panodan FDP [DATAE]; and
Glyceryl-Lacto Esters of Fatty Acids (solid) - Durlac 100 W [GLE].

Controls

Sucrose Polyester (Oleate) [SPE]; Peanut Oil

The degree of anal leakage is determined on a scale of 0 to 4, defined as follows:

0=None; 1=Trace; 2=Slight; 3=Moderate; 4=Severe

Scoring was conducted twice daily.

The results are reported in the following Table 2:

TABLE 2

| DIET | AVERAGE SCORE | % EFFECTIVENESS |
|---|---|---|
| 1. Lecithin | 1.56 | 61.00 |
| 2. MD 10% | 0.69 | 82.75 |
| 3. EMD | 1.02 | 74.50 |
| 4. POLY 60 | 1.08 | 73.00 |
| 5. SSL | 1.46 | 63.50 |
| 6. MG soft plastic | 2.37 | 40.75 |
| 7. MG plastic | 2.10 | 47.50 |
| 8. MG bead | 0.85 | 78.75 |
| 9. SEFA | 1.07 | 73.25 |
| 10. DATAE | 1.39 | 64.75 |
| 11. GLE | 0.26 | 93.50 |
| 12. SPE - control | 2.58 | 35.50 |
| 13. PEANUT OIL - control | 0.00 | 100.00 |

What follows is two more examples.

EXAMPLE III

A feeding study was done to determine the disposition of anal leakage in rats fed with a fat substitute material containing various emulsifiers or gums as an anti-anal leakage agent. The rats were female, of the Sprague Dawley species, weighing 150 to 200 grams. The rats were fed Teklad fat free rat chow, admixed with sucrose polyester (oleic acid esters) as a fat substitute material and the specific emulsifier or gum to be tested. The combined sucrose polyester and the specific emulsifier or gum being tested comprised 16% by weight of the mixture, based on the weight of the fat free Teklad rat chow. The specific emulsifier or gum being tested comprised 20% by weight of the combined sucrose polyester and emulsifier or gum.

The degree of anal leakage resulting was determined once each day, and scored on a scale of 0 to 4, defined as follows: 0=no anal leakage; 1=trace anal leakage; 2=slight anal leakage; 3=mild anal leakage; and 4=severe anal leakage.

Each formulation of feed, sucrose polyester, and specific emulsifier or gum being tested was fed to each of a group of five rats for a period of ten days. The anal leakage over the period of the experiment was scored for each rat, and then averaged over the ten-day period. The average scores were also converted to a percent effectiveness, as follows: an average score of 0=100% effectiveness; an average score of 1=75% effectiveness; an average score of 2=50% effectiveness; an average score of 3=25% effectiveness; and an average score of 4=0% effectiveness. One feed formulation contained 100% of the sucrose polyester (oleic acid esters), with no added emulsifier or gum, as a control.

The following emulsifiers or gums were tested:

Acetylated Monoglycerides—Cetodan, available from Grindsted Chemical Corp.;
Hydroxylated Lecithin ("Lecithin");
Xanthan Gum;
Sodium Hexa Meta Phosphate ("SHMP");
Carrageenan Gum;
Pectin;
Mono-, Di-Glycerides 20%—Emuldan, solid ("Emuldan"); and
Sucrose Polyester ("SPE") (Control).

The results achieved from feeding studies for formulations containing each of these emulsifiers or gums are listed below in Table 3.

TABLE 3

| EMULSIFIER/GUM | AVERAGE SCORE | % EFFECTIVENESS |
|---|---|---|
| Acetylated Monoglycerides | 0.26 | 93.50 |
| Lecithin | 1.66 | 59.50 |
| Xanthan Gum | 1.16 | 71.00 |
| SHMP | 2.54 | 36.50 |
| Carrageenan Gum | 1.72 | 54.50 |
| Pectin | 2.22 | 44.50 |
| Emuldan 20% | 0.00 | 100.00 |
| SPE | 3.00 | 25.00 |

Acetylated monoglycerides and Emuldan 20% were found to be effective anti-anal leakage agents. Xanthan gum was also found to be a suitable anti-anal leakage agent at this concentration. Hydroxylated lecithin indicated promise as being an effective anti-anal leakage agent at higher percentages.

EXAMPLE IV

A feeding study was done to determine the disposition of anal leakage in rats fed with a fat substitute material containing various emulsifiers or gums as an anti-anal leakage agent. The rats were female, of the Sprague Dawley species, weighing 150 to 200 grams. The rats were fed Teklad fat free rat chow, admixed with sucrose polyesters (oleate) as a fat substitute material and the specific emulsifier or gum to be tested. The combined sucrose polyester and the specific emulsifier or gum being tested comprised 16% by weight of the mixture, based on the weight of the fat free Teklad rat chow. A specific emulsifier or gum being tested comprised 20% by weight of the combined sucrose polyester and emulsifier or gum, except in the case of the mono-, di-glycerides (Emuldan). The Emuldan comprised 20%, 10% or 5% of the combined sucrose polyester and Emuldan, as indicated.

The degree of anal leakage resulting was determined once each day, and scored on a scale of 0 to 4, defined as follows: 0=no anal leakage; 1=trace anal leakage; 2=slight anal leakage; 3=mild anal leakage; and 4=severe anal leakage.

Each formulation of feed, sucrose polyester, and specific emulsifier or gum being tested was fed to each of a group of five rats for a period of ten days. The anal leakage over the period of the experiment was scored for each rat, and then averaged over the ten day period. The average scores were also converted to a percent effectiveness, as follows: an average score of 0=100% effectiveness; an average score of 1=75% effectiveness; an average score of 2=50% effectiveness; an average score of 3=25% effectiveness; and an average score of 4=0% effectiveness.

The following emulsifiers and gums were tested:

Mono-, Di-Glycerides 10%—Emuldan ("Emuldan 10%");
Gum Arabic;
Poly Glycerol Lactic Acid Ester—Lactodan, available from Grindsted Chemical Corp. ("Lactodan");
Mono-, Di-Glycerides 5%—Emuldan ("Emuldan 5%");
Propylene Glycol Mono Stearate ("PGMS");
Sucrose Polyester ("SPE");
Guar Gum;
Poly Aldo Deca Glycerol Deca Stearate Palmitate mixture, available from Lanza Chemical Corp. ("Poly Aldo DGDSP");
Poly Aldo Hexa Glycerol Mono Palmitate, available from Lanza Chemical Corp. ("Poly Aldo HGMP");
Gellan Gum, available from Kelco, Inc.; and
Mono-, Di-Glycerides 20%—Emuldan ("Emuldan 20%").

Results from feeding studies conducted with these emulsifiers and gums are listed below in Table 4.

TABLE 4

| EMULSIFIER/GUM | AVERAGE SCORE | % EFFECTIVENESS |
|---|---|---|
| Emuldan 10% | 0.74 | 81.50 |
| Gum Arabic | 3.36 | 16.00 |
| Lactodan | 0.44 | 90.00 |
| Emuldan 5% | 2.59 | 44.00 |
| PGMS | 0.00 | 100.00 |
| SPE | 3.30 | 17.50 |
| Guar Gum | 2.10 | 47.00 |
| Poly Aldo DGDSP | 2.74 | 31.50 |
| Poly Aldo HGMP | 2.74 | 31.00 |
| Gellan Gum | 1.44 | 64.00 |
| Emuldan 20% | 0.00 | 100.00 |

Emuldan at concentrations of about 10 to 20%, Lactodan, and propylene glycol mono stearate were found to be effective anti-anal leakage agents. Based on the performance of propylene glycol mono stearate, poly glycerol mono stearates in general are suspected of being suitable anti-anal leakage agents. Gellan gun showed promise as an anti-anal leakage agent if included at higher concentrations (i.e., greater than 20%).

While the preferred embodiments of the present invention have been described, other modifications may be made thereto and other embodiments may be devised within the spirit of the invention and scope of the appended claims.

The embodiments of the invention in which an exclusive property or privilege is claimed are defined as follows:

1. A fat substitute composition, comprising: an edible, substantially non-digestible fat substitute material having a melting point of about 37° C. or less, in combination with an emulsifier as an anti-laxative agent selected from the group consisting of: non-liquid polyglyceryl esters of at least one $C_1$-$C_{18}$ fatty acid; non-liquid $C_1$-$C_{18}$ fatty acid mono- and di-glycerides; ethoxylated mono- and di-glycerides; sorbitan esters of at least one $C_1$-$C_{18}$ fatty acid; glyceryl-lacto esters of at least one $C_1$-$C_{18}$ fatty acid; acetylated monoglycerides; poly glycerol lactic acid ester; propylene glycol mono stearate; xanthan gum; and mixtures thereof, said anti-laxative agent being contained in said composition at a level of at least 10% by weight of said fat substitute material to reduce leakage of said non-digestible fat substitute material through the anal sphincter of a mammal.

2. A composition according to claim 1, wherein said anti-laxative agent is an acetylated monoglyceride.

3. A composition according to claim 1, wherein said anti-laxative agent is propylene glycol mono stearate.

4. A composition according to claim 1, wherein said anti-laxative agent is poly glycerol lactic acid ester.

5. A composition according to claim 1, wherein said anti-laxative agent is xanthan gum.

6. A composition according to claim 1, wherein said anti-laxative agent is non-liquid $C_1$-$C_{18}$ fatty acid mono- and di-glycerides.

7. A composition according to claim 1, wherein said anti-laxative agent is included at a level of 10 to 25% by weight based on the weight of the fat substitute material.

8. A composition according to claim 1, wherein said fat substitute material is a polyol fatty acid polyester, having at least 4 fatty acid ester groups, wherein the polyol is a sugar or sugar alcohol containing 4 to 8 hydroxyl groups and each fatty acid has from about 8 to about 18 carbon atoms.

9. A composition according to claim 1, wherein said fat substitute material is a combination of hexa-, hepta-, and octa-esters of sucrose with fatty acids having from about 8 to about 18 carbon atoms.

10. The fat substitute composition of claim 1, wherein the anti-laxative agent is a non-liquid polyglyceryl ester of at least one C1-C18 fatty acid.

11. The fat substitute composition of claim 1, wherein the anti-laxative agent is an ethoxylated mono- or di-glyceride.

12. The fat substitute composition of claim 1, wherein the anti-laxative agent is a sorbitan ester of at least one C1-C18 fatty acid.

13. The fat substitute composition of claim 1, wherein the anti-laxative agent is a glyceryl-lacto ester of at least one C1-C18 fatty acid.

14. A method of reducing anal leakage in a mammal after ingestion by said mammal of a food composition comprising an edible, substantially non-digestible fat substitute material having a melting point of about 37° C. or less, comprising:
  incorporating into said food composition an emulsifier as an anti-laxative agent, wherein the emulsifier is included at a level of at least 10% by weight of said fat substitute material and comprises selected from the group consisting of: non-liquid polyglyceryl esters of at least one $C_1$-$C_{18}$ fatty acid; non-liquid $C_1$-$C_{18}$ fatty acid mono- and di-glycerides; ethoxylated $C_1$-$C_{18}$ fatty acid mono- and di-glycerides; sorbitan esters of at least one $C_1$-$C_{18}$ fatty acid; glyceryl-lacto esters of at least one $C_1$-$C_{18}$ fatty acid; acetylated monoglycerides; poly glycerol lactic acid ester; propylene glycol mono stearate; xanthan gum; and mixtures thereof.

15. A method according to claim 10, wherein said anti-laxative agent is non-liquid $C_1$-$C_{18}$ fatty acid mono- and di-glycerides.

16. A method according to claim 10, wherein said anti-laxative agent is included at a level of from 10 to 25% by weight based on the weight of said fat substitute material contained in said food composition.

17. A method according to claim 14, wherein said anti-laxative agent is an acetylated monoglyceride.

18. A method according to claim 14, wherein said anti-laxative agent is poly glycerol lactic acid ester.

19. A method according to claim 14, wherein said anti-laxative agent is propylene glycol mono stearate.

20. A method according to claim 14, wherein said anti-laxative agent is xanthan gum.

21. A method according to claim 14, wherein said fat substitute material is a polyol fatty acid polyester having at least 4 fatty acid ester groups, wherein the polyol is a sugar or sugar alcohol containing 4 to 8 hydroxyl groups and each fatty acid has from about 8 to 18 carbon atoms.

22. A method according to claim 14, wherein said fat substitute material is a combination of hexa-, hepta-, and octa-esters of sucrose with fatty acids having from about 8 to about 18 carbon atoms.

23. A fat substitute composition, comprising: an edible, substantially non-digestible fat substitute material having a melting point of about 37° C. or less, in combination with an emulsifier as an anti-laxative agent selected from the group consisting of: non-liquid polyglyceryl esters of at least one $C_1$-$C_{18}$ fatty acid; non-liquid $C_1$-$C_{18}$ fatty acid mono- and di-glycerides; ethoxylated mono- and di-glycerides; sorbitan esters of at least one $C_1$-$C_{18}$ fatty acid; glyceryl-lacto esters of at least one $C_1$-$C_{18}$ fatty acid; acetylated monoglycerides; poly glycerol lactic acid ester; propylene glycol mono stearate; xanthan gum; and mixtures thereof, said anti-laxative agent being contained in said composition at a level of greater than 5% by weight of said fat substitute composition to reduce leakage of said non-digestible fat substitute material through the anal sphincter of a mammal.

24. A method of reducing anal leakage in a mammal after ingestion by said mammal of a food composition comprising an edible, substantially non-digestible fat substitute material having a melting point of about 37° C. or less, comprising:
  incorporating into said food composition an emulsifier as an anti-laxative agent, wherein the emulsifier is present at a level of greater than 5% by weight of said food composition and is selected from the group consisting of: non-liquid polyglyceryl esters of at least one $C_1$-$C_{18}$ fatty acid; non-liquid $C_1$-$C_{18}$ fatty acid mono- and di-glycerides; ethoxylated $C_1$-$C_{18}$ fatty acid mono- and di-glycerides; sorbitan esters of at least one $C_1$-$C_{18}$ fatty acid; glyceryl-lacto esters of at least one $C_1$-$C_{18}$ fatty acid; acetylated monoglycerides; poly glycerol lactic acid ester; propylene glycol mono stearate; xanthan gum; and mixtures thereof.

25. A low calorie food composition comprising fat ingredients and nonfat ingredients, wherein greater than 40% by weight of the fat ingredients comprise:
  an edible, substantially non-digestible fat substitute material having a melting point of about 37° C. or less that exhibits a laxative effect, in combination with an emulsifier as an anti-laxative agent selected from the group consisting of: non-liquid polyglyceryl esters of at least one $C_1$-$C_{18}$ fatty acid; non-liquid $C_1$-$C_{18}$ fatty acid mono- and di-glycerides; ethoxylated mono- and di-glycerides; sorbitan esters of at least one $C_1$-$C_{18}$ fatty acid; glyceryl-lacto esters of at least one $C_1$-$C_{18}$ fatty acid; acetylated monoglycerides; poly glycerol lactic acid ester; propylene glycol mono stearate; xanthan gum; and mixtures thereof, said anti-laxative agent being contained in said food composition in an amount sufficient to reduce leakage of said non-digestible fat substitute material through the anal sphincter of a mammal.

26. The low calorie food composition of claim 25, wherein greater than 60% of the fat ingredients by weight comprise the combined fat substitute material and anti-laxative agent.

27. The low calorie food composition of claim 25, wherein the anti-laxative agent is included at a level of at least 10% by weight of the fat substitute material.

28. A fat substitute composition, comprising:
an edible, substantially non-digestible fat substitute material having a melting point of about 37° C. or less, in combination with an emulsifier as an anti-laxative agent, wherein the emulsifier comprises a digestible polyol fatty acid polyester having at most 3 fatty acid ester groups, wherein the polyol is a sugar or sugar alcohol containing from 4 to 8 hydroxyl groups and wherein each acid group has from about 8 to about 18 carbon atoms, said anti-laxative agent being in said composition at a level of at least 10% by weight of said fat substitute material to reduce leakage of said fat material through the anal sphincter of a mammal.

29. A composition according to claim 28, wherein said polyol is selected from the group consisting of glucose and sucrose.

30. A composition according to claim 29, wherein said anti-laxative agent is a member selected from the group consisting of mono-, di-, and tri-palmitates and stearates of sucrose.

31. A composition according to claim 29, wherein said anti-laxative agent is a member selected from the group consisting of methyl glucoside mono-, di-, and tri-palmitates and stearates.

32. A composition according to claim 28, wherein said fat substitute material is a polyol fatty acid polyester having at least 4 fatty acid ester groups, wherein the polyol is a sugar or sugar alcohol containing 4 to 8 hydroxyl groups and each fatty acid has from about 8 to about 18 carbon atoms.

33. A composition according to claim 32, wherein said fat substitute material is a combination of hexa-, hepta-, and octa-esters of sucrose with fatty acids having from about 8 to about 18 carbon atoms.

34. A method of reducing anal leakage in a mammal after ingestion by said mammal of a food composition comprising an edible, substantially non-digestible fat substitute material having a melting point of about 37° C. or less, comprising:
incorporating into said food composition an emulsifier as an anti-laxative agent, wherein said emulsifier is included at a level of at least 10% by weight of said fat substitute material and comprises a digestible polyol fatty acid polyester having at most 3 fatty acid ester groups, wherein the polyol is a sugar or sugar alcohol containing from 4 to 8 hydroxyl groups and wherein each fatty acid group has from about 8 to about 18 carbon atoms.

35. A fat substitute composition, comprising:
an edible, substantially non-digestible fat substitute material having a melting point of about 37° C. or less, in combination with an emulsifier as an anti-laxative agent, wherein the emulsifier comprises a digestible polyol fatty acid polyester having at most 3 fatty acid ester groups, wherein the polyol is a sugar or sugar alcohol containing from 4 to 8 hydroxyl groups and wherein each acid group has from about 8 to about 18 carbon atoms, said agent being contained in said fat substitute composition at a level of greater than 5% by weight of said fat substitute composition to reduce leakage of said fat substitute material through the anal sphincter of a mammal.

36. A method of reducing anal leakage in a mammal after ingestion by said mammal of a food composition comprising an edible, substantially non-digestible fat substitute material having a melting point of about 37° C. or less, comprising:
incorporating into said food composition an emulsifier as an anti-laxative agent, wherein said emulsifier is included at a level of greater than 5% by weight of said food composition and is a digestible polyol fatty acid polyester having at most 3 fatty acid ester groups, wherein the polyol is a sugar or sugar alcohol containing from 4 to 8 hydroxyl groups and wherein each fatty acid group has from about 8 to about 18 carbon atoms, said anti-laxative agent being contained in said food composition in an amount sufficient to reduce leakage of said fat substitute material through the anal sphincter of a mammal.

37. A low calorie food composition comprising fat ingredients and nonfat ingredients, wherein greater than 40% by weight of the fat ingredients comprise:
an edible, substantially non-digestible fat substitute material having a melting point of about 37° C. or less that exhibits a laxative effect, in combination with an emulsifier as an anti-laxative agent, wherein the emulsifier comprises a digestible polyol fatty acid polyester having at most 3 fatty acid ester groups, wherein the polyol is a sugar or sugar alcohol containing from 4 to 8 hydroxyl groups and wherein each acid group has from about 8 to about 18 carbon atoms, said agent being in said food composition in an amount sufficient to reduce leakage of said fat substitute material through the anal sphincter of a mammal.

38. The low calorie food composition of claim 37, wherein greater than 60% of the fat ingredients by weight comprise the combined fat substitute material and anti-laxative agent.

39. The low calorie food composition of claim 37, wherein the anti-laxative agent is included at a level of at least 10% by weight of the fat substitute material.

* * * * *